United States Patent
France

(10) Patent No.: US 12,220,497 B2
(45) Date of Patent: Feb. 11, 2025

(54) MATERIALS AND METHODS FOR DECONTAMINATING ANIMAL INTEGUMENT

(71) Applicant: TDA Research, Inc, Wheat Ridge, CO (US)

(72) Inventor: Christopher Brian France, Arvada, CO (US)

(73) Assignee: TDA Research, Inc., Golden, CO (US)

( * ) Notice: Subject to any disclaimer, the term of this patent is extended or adjusted under 35 U.S.C. 154(b) by 870 days.

(21) Appl. No.: 17/385,359

(22) Filed: Jul. 26, 2021

(65) Prior Publication Data

US 2022/0080072 A1    Mar. 17, 2022

Related U.S. Application Data

(60) Provisional application No. 63/079,302, filed on Sep. 16, 2020.

(51) Int. Cl.
*A61L 2/26*      (2006.01)
*A61L 2/00*      (2006.01)
*A61L 2/16*      (2006.01)

(52) U.S. Cl.
CPC .............. *A61L 2/26* (2013.01); *A61L 2/0082* (2013.01); *A61L 2/16* (2013.01); *A61L 2202/17* (2013.01); *A61L 2202/20* (2013.01)

(58) Field of Classification Search
CPC ...... A01K 13/001; A01K 13/00; A61Q 17/00; A61L 2202/20; A61L 2/26
See application file for complete search history.

(56) References Cited

U.S. PATENT DOCUMENTS

| | | | |
|---|---|---|---|
| 2004/0007251 A1* | 1/2004 | Koenig | C11D 3/382 15/104.93 |
| 2006/0204558 A1* | 9/2006 | Kantner | A61K 31/22 424/443 |
| 2008/0085848 A1* | 4/2008 | Johnston | A62D 3/30 510/110 |

(Continued)

OTHER PUBLICATIONS

Canine Decontamination, Lori E. Gordon, DVM (Year: 2017).*

(Continued)

*Primary Examiner* — Morgan T Jordan
*Assistant Examiner* — Shada Mohamed Alghailani
(74) *Attorney, Agent, or Firm* — Brian J. Elliott; Grace B. Clinger

(57) ABSTRACT

A method for decontaminating the outer integument of an animal without transferring contamination to the inner integument of the animal where the hazard can interact with the skin and harm the animal further. The animal has either fur, hair, or feathers and the inner integument is the skin and a skin-hazard material is present on the outer integument (the fur, hair, or feathers). The method uses a first porous dry wipe to sequester the skin-hazard material away from the contaminated animal by either wiping, blotting or rubbing the outer integument of the contaminated animal. The method avoids using free-flowing liquid in contact with the inner integument of the contaminated animal, and does not promote a liquid-phase transfer of the skin-hazard material from the outer integument to the inner integument.

20 Claims, 14 Drawing Sheets
(3 of 14 Drawing Sheet(s) Filed in Color)

(56) References Cited

U.S. PATENT DOCUMENTS

| | | | | |
|---|---|---|---|---|
| 2013/0338420 A1* | 12/2013 | Willey | ................... | A62D 3/36 |
| | | | | 588/318 |
| 2015/0157887 A1* | 6/2015 | Chilcott | ............... | C08F 122/02 |
| | | | | 523/105 |
| 2015/0182093 A1* | 7/2015 | Fridlin | ................... | A47L 13/19 |
| | | | | 15/227 |

OTHER PUBLICATIONS

Bartlet-Hunt et al. (2008) A Review of Chemical Warfare Agent Simulants for the Study of Environmental Behavior. Critical Reviews in Environmental Science and Technology, 2008.

Chilcott, R. P., and Amlot (2015) Prism Guidance for Chemical Incidents vol. 3: Operational Guidance for Mass Casualty Disrobe and Decontamination.

Gordon, L (2017) Canine Decontamination Guidelines for Emergency, Gross, and Technical Decontamination of the Urban Search & Rescue Canine.

\* cited by examiner

2-Chloroethyl Phenyl Sulfide (CEPS)   Methyl Salicylate (MS)

| Test Solutions (concentration, ratio) | Orange Glo Germ(R) | CEPS | MS |
|---|---|---|---|
| Mane&Tail (30:1; 50:1) | 20s | 46s | 1m11 |
| Chlorhexidine (30:1; 50:1) | 4s | 50s | 1m30s |
| Chlorhexidine (Neat; 50:1) | 14s | 1m | 40s |
| Hibiclens (30:1; 50:1) | 20s | 1m | 1m20s |
| Hibiclens (Neat; 50:1) | >4hrs | 11m30s | 10m |
| Hibiclens (Neat; 50:5) | - | Solidified | Solidified |
| Dawn (30:1; 50:1) | 10s | 1m | 1m |
| Palmolive (30:1; 50:1) | 17s | 1m | 1m |
| SSDX (30:1; 50:1) | 30s | 2m30s | 4m20s |

Fig. 7

| Decontaminant | % recovery | % decon |
|---|---|---|
| Direct Injection into Acetone | 102.13% | |
| Contamination of membrane, extraction | 95.40% | |
| Water | 85.90% | 14.10% |
| Mane & Tail Conditioner 30:1 | 87.82% | 12.18% |
| 30:1 Hibiclens | 85.69% | 14.31% |
| neat Hibiclens | 78.58% | 21.42% |
| Mane & Tail Shampoo 30:1 | 85.14% | 14.86% |
| 1oz/gallon chlorohexidine | 80.37% | 19.63% |
| 30:1 Palmolive | 85.69% | 14.31% |
| 30:1 Dawn Ultra | 81.47% | 18.53% |
| 30:1 SSDX-12 | 81.69% | 18.31% |

Fig. 8

| Decontaminant | % recovery | % decon |
|---|---|---|
| Direct Injection into Acetone | 102.38% | |
| Contamination of membrane, extraction | 96.99% | |
| contamination of membrane, water wash, extraction | 98.01% | 1.99% |
| Mane & Tail Conditioner 30:1 | 95.54% | 4.46% |
| 30:1 Hibiclens | 94.44% | 5.56% |
| neat Hibiclens | 92.32% | 7.68% |
| Mane & Tail Shampoo 30:1 | 92.78% | 7.22% |
| 1oz/gallon chlorohexidine | 94.10% | 5.90% |
| 30:1 Palmolive | 86.54% | 13.46% |
| 30:1 Dawn Ultra | 84.63% | 15.37% |
| 30:1 SSDX-12 | 88.16% | 11.84% |

Fig. 9

| Decontaminant | % recovery | % decon |
|---|---|---|
| Contamination of fur, extraction | 102.26% | |
| Water | 20.10% | 79.90% |
| Mane & Tail Conditioner 30:1 | 32.20% | 67.80% |
| 30:1 Hibiclens | 5.24% | 94.76% |
| neat Hibiclens | Solidified | Solidified |
| Mane & Tail Shampoo 30:1 | 3.75% | 96.25% |
| 1oz/gallon chlorohexidine | 6.18% | 93.82% |
| 30:1 Palmolive | 9.07% | 90.93% |
| 30:1 Dawn Ultra | 2.39% | 97.61% |
| 30:1 SSDX-12 | 1.96% | 98.04% |

Fig. 10

| Decontaminant | % recovery | % decon |
|---|---|---|
| Contamination of fur, extraction | 95.88% | |
| water | 74.58% | 25.42% |
| Mane & Tail Conditioner 30:1 | 22.58% | 77.42% |
| 30:1 Hibiclens | 6.71% | 93.29% |
| neat Hibiclens | Solidified | Solidified |
| Mane & Tail Shampoo 30:1 | 16.77% | 83.23% |
| 1oz/gallon chlorohexidine | 41.64% | 58.36% |
| 30:1 Palmolive | 36.38% | 63.62% |
| 30:1 Dawn Ultra | 25.42% | 74.58% |
| 30:1 SSDX-12 | 37.73% | 62.27% |

Fig. 11

MATERIALS AND METHODS FOR DECONTAMINATING ANIMAL INTEGUMENT

STATEMENT REGARDING FEDERALLY SPONSORED RESEARCH OR DEVELOPMENT

This invention was made using U.S. government funding through the U.S. Army SBIR Phase I contract #W911NF-20-P-0022. The government has certain rights in this invention.

FIELD OF THE INVENTION

The field of the invention relates to materials and methods for decontaminating the integument of vertebrates, including canines, horses, and humans. The field also relates to a kit that can be used for decontaminating integument. In certain aspects, the field relates to the removal of highly toxic chemical compounds that are deposited on an animal's integument, for example a working dog's fur, in a manner that does not promote transport of the highly toxic chemical compound towards the animal's permeable skin layer, and in a manner that does not promote the highly toxic chemical compound from harming or killing the animal.

BACKGROUND

The state-of-the-art procedure for removing toxic chemical contamination, particularly on people or on animals, is to use copious amounts of soap and water. For example, soap and water wash is specified for dog decon, as described in FM (2004) and Gordon (2017). Procedures for human decon from chemical warfare (CW) agents also focus on large amounts of soap and water (Chilcott and Amlot 2015).

When dealing with wildlife contaminated with a chemical compound or other harmful material substance, the standard procedure is washing with water and dish detergent. A familiar example is wild birds that have become contaminated with oil from an oil spill. The established procedure uses large quantities of warm soapy water. Birds are washed in tubs of warm soapy water. When the water gets dirty, they are moved to the next tub. They keep getting moved to clean tubs, until all the oil is off them and the water is clear. Sea otters and fur seals have warm soapy water poured on them and massaged into their thick hair coats. Other mammals and sea turtles usually have soap directly placed on the oiled areas and scrubbed. Then they are rinsed off. This step is very important, because all the soap needs to come off, or the animals' fur or feathers may not go back to normal and they may not be able to become waterproof. It takes a long time to clean an animal. Birds may take over an hour to wash and rinse, and marine mammals may take several hours.

The established procedure suffers from the limitation that it is time-consuming and requires physical resources and labor that may not be available. In addition, the established procedure specifies dish detergent; however, dish detergent is optimized for removal of common food-related solids, and not for removal of hydrophobic materials, such as chemical warfare agents. The established procedure also suffers from the limitation that is can transfer hazardous materials from fur (or feathers) to direct contact with skin, which can be permeable to hazardous materials and allow them to enter internal tissue or the blood steam.

A cleaning and decontaminating procedure is desirable for dogs, and in particular for working dogs, which may encounter a range of hazardous materials. Military working dogs (MWDs) have been an integral part of the US military since its inception. Currently, these working dogs are assigned to every branch of the US military and are deployed worldwide. These dogs are frequently deployed into military field environments that can at times be quite hazardous. Current decontamination protocols for military working dogs are limited and fail to address the wide variety of different chemical exposure scenarios that exist in the military theater. Protecting military working dogs from exposure to hazardous chemicals and materials is especially challenging because protective equipment in the form of inhalation masks and suits essentially blocks a MWD's ability to perform key functions (detecting, smelling, warning and biting). While a canine's paws and face are areas for rapid exposure, the canine's fur is its first line of defense against less than immediately toxic exposures. Existing taught cleaning methods involving copious amounts of soapy water either poured over or used to submerse the animal (a bath). These methods lead to the unfortunate potential to move the hazardous material from the fur to the skin (where they could then be absorbed and injure or kill the animal).

BRIEF SUMMARY OF THE INVENTION

The present invention solves the limitations of the prior art and provides materials and methods to remove undesirable or hazardous chemicals from an animal. For the purposes of the present specification and the accompanying claims, the term animal means a live vertebrate having hair, fur, feathers, scales, horns or any structure comprising keratin on at least part of its body. In preferred embodiments the animal is a dog, a non-limiting example being a military working dog.

As described in the Background section, the existing teaching and known decontaminating procedures, particularly for contaminated animals or people, is the use of large quantities of soap and water. Advantages of the present invention include not transferring hazardous materials (from hair, fur) to the skin surface and also decreasing the quantity of cleaning materials required during the decontaminating procedure, thus also decreasing the amount of waste generated that might need to be handled as hazardous waste itself.

An additional advantage is realized in decontaminating items having an outer surface and an inner surface. In many cases the contamination will initially be deposited on the outer surface. In that case, we demonstrate that the use of wipes is effective in removing contamination from the outer surface and avoiding transfer to the inner surface. For example, if a dog encounters contamination in the form of a liquid or powder solid, that contamination will initially reside on the dog's fur. The use of wipes can remove the contamination from the fur (the outer surface) and prevent transfer to the skin (the inner surface). In contrast, the standard procedure of washing with soap and water will suspend the contamination in the soapy water, and inevitably some of it will contact the skin. It is particularly desirable to prevent transfer of the contaminant to the inner surface (dog's skin) when the contaminant is a toxic material that can be absorbed through the skin (a contact hazard). More generally, it is desirable to remove contamination from the outer surface because contamination on the outer surface is more accessible and more readily removed.

In another embodiment, the present invention is an improved method to remove undesirable or hazardous materials from a living organism. The materials and methods of the present invention are particularly effective in removing undesirable or hazardous materials from an organism having hair, fur, feathers, scales, horn or any structure comprising keratin on at least part of its body.

In the present invention the toxic chemical is transferred directly from the dog's fur to a wipe. This procedure minimizes the opportunity for the toxic chemical to come in contact with the animal's skin, where it could be absorbed into the animal's body and cause illness or death. In the experiments described in the Detailed Description of the Invention we have found that chemical agents remain on or in the animal's hair and do not wick to the skin.

In one embodiment the present invention utilizes a wet wipe with a small amount of surfactant and water to wipe the animal's fur without allowing the solution to wet the fur down to the animal's skin. A dry wipe then follows, to absorb the wet wipe materials which will have dissolved the chemical agent. The dry wipe draws the agent and solution off the fur and away from the animal's skin, preventing poisoning.

In another embodiment the present invention utilizes a dry wipe followed by a wet wipe with a small amount of surfactant and water to wipe the animal's fur without allowing the solution to wet the fur down to the animal's skin. Optionally a second dry wipe then follows the wet wipe, to absorb the wet wipe materials which will have dissolved the chemical agent. The dry wipe draws the agent and solution off the fur and away from the animal's skin, preventing poisoning.

In contrast, the established current state of the art procedure uses copious amounts of soap and water wash, in which the toxic chemical is mobilized by a detergent. In this situation the wash water containing the toxic chemical comes in contact with the animal's skin. The toxic chemical can then spread onto the skin and be absorbed by the animal. It is clear that the prior art for decontamination (especially for highly toxic agents), using large quantities of soap and water, teaches away from our approach, which has no water of a very minimal amount of water, only enough to form a wetted or a damp wipe. Procedures for human decon from chemical warfare (CW) agents also focus on large amounts of soap and water (Chilcott and Amlot 2015).

The present invention may be used as a first step to remove the bulk of contamination in a controlled manner to avoid skin contact or transfer of the hazardous material to skin, followed by a soap and water wash if desirable. In another embodiment for animal decon, the present invention can be used for preliminary decontamination before conducting a complete animal wash. Use of the wipe decon will minimize the dangers to the animal from poisoning but also minimize the hazard to the handler washing the animal who could easily come in contact with the toxic substance and become poisoned by the agent.

An additional advantage to this procedure is that it produces a minimal amount of solid waste for disposal. After decontamination the used wipes can be placed into a bag and then safely stored or transported for later disposal. In contrast, soap and water wash produces a volume of liquid containing the soap and toxic chemicals, which is more difficult to store, transport and dispose of. Because soap and water removes but does not destroy or neutralize a toxic contaminant, use of soap and water can produce a large volume of liquid that still contains the contaminant and is potentially hazardous.

Yet another advantage of this procedure is that the materials for decontamination have a small volume (for example 0.5 ounce, 1 ounce, 5 mL, 10 mL, 15 mL, or less than 5 mL), so that the system is readily transportable. In contract, soap and water wash of a dog requires providing a significant volume of water, which may not be readily available.

The wipes used in this invention are flexible pieces of material, including paper, woven or nonwoven cloth, woven or nonwoven microfiber cloth, and flexible flat pieces of plastic. The wipes may be used dry (without added liquid), or with added liquid. The added liquid may be water, water with a detergent or surfactant, or a solvent with suitable properties, such as turpentine. When a liquid is used, it is added in limited quantity, so that the liquid remains in the wipe normally and is only sparingly transferred to the fur to the animal's skin during a wiping or blotting procedure. A small amount of liquid will transfer out of the wetted wipe to the strands of the fur, but the amount of liquid will not be large enough to full saturate the fur or run down the fur strands and contact the skin.

The wipes may be applied once or more than once (twice, three times, four times, five times, etc.). For example, the procedure used can involve wiping a dog's fur with a dry wipe, wiping the fur with a wet wipe, or both of the above in sequence. An example would be wiping a dog's fur with a dry wipe to remove any readily accessible contaminant, then wiping the fur with a wet wipe to remove additional contaminant, and then wiping the fur with a dry wipe to remove more contaminant, and also to remove any liquid that might remain from the wet wipes. Other sequences may also be used. If multiple wipes are used, they may be made of different materials. One example is to use a polymer microfiber wipe as the dry wipe and a paper or cotton fiber cloth as the wet wipe. Microfiber wipes of polymers such as polypropylene are effective in absorbing non-polar materials from surfaces. Paper and cotton fiber wipes are effective in absorbing water and soap in quantities that can aid removal of the undesirable material without releasing excess liquid that can spread the undesirable material to the skin.

The present invention teaches a method for removing contamination from a live organism using a wipe, optionally where soap and water wash is not used. Or, where the wipe is a flexible piece of material, including paper, woven or nonwoven cloth, fabric, woven or nonwoven microfiber cloth, and flexible pieces of polymer, either smooth or textured. The wipe may be dry or wet, or wetted with a minimal quantity of water and surfactant (the surfactant may be a nonionic surfactant, optionally a mixture of nonionic surfactants as disclosed in U.S. Pat. No. 9,295,865 and referred to in this specification as SSDX-12®). Multiple wipes may be used (wet, dry, in any sequence).

The present invention teaches an effective method for decontaminating the outer integument of an animal without transferring contamination to the inner integument of the animal, the method comprising: providing a contaminated animal, wherein the contaminated animal has an outer integument comprising of either fur, hair, or feathers; wherein the animal has an inner integument comprising skin; and wherein a skin-hazard material is present on the outer integument; providing a first porous dry wipe; using the first porous dry wipe to sequester the skin-hazard material away from the contaminated animal by either wiping, blotting or rubbing the outer integument of the contaminated animal; not using free-flowing liquid in contact with the inner integument of the contaminated animal; and not promoting a liquid-phase transfer of the skin-hazard material from the outer integument to the inner integument.

In optional embodiments: the method, further comprises: not using free-flowing liquid in contact with the inner integument, wherein the free-flowing liquid comprises a mixture of soap and water; and not submersing any part of the contaminated animal in a liquid bath.

In further embodiments the method further comprises: wherein, the skin-hazard material is a skin contact-hazard material, and effectively decontaminating the contaminated animal, wherein effectively decontaminating means reducing the presence of the skin-contact hazard material on the outer integument to a level below a contact-hazard level for the contaminated animal, and while not transferring an amount of the skin contact-hazard material, which is above a contact-hazard level for the first species, from the outer integument to the inner integument.

In another embodiment the method further comprises: using a wetted wipe to sequester at least a portion of the skin contact-hazard material away from the contaminated animal by either wiping, blotting or rubbing the outer integument of the contaminated animal; using the wetted wipe to deposit a skin-hazard material solubilizing agent onto the outer integument; and using a second porous dry wipe after using the wetted wipe to sequester at least a portion of the skin-hazard material away from the contaminated animal by either wiping, blotting or rubbing the outer integument containing the skin-hazard material solubilizing agent, of the contaminated animal. Optionally, the method further comprises: trimming or cutting a portion of the outer integument off of the contaminated animal.

In an optional embodiment, the using the wetted wipe step happens after the using the first dry wipe step.

In certain embodiments, the wetted wipe contains non-ionic surfactants, and preferably the wetted wipe contains an aqueous solution containing linear, C12, secondary alcohol alkoxylate, polyoxyethylene (4) sorbitan monolaurate, octyldimethylamine oxide, and cocoamidopropyl dimethlamine oxide. For example, the surfactant solution is preferably a diluted (5% in water) solution of the surfactant formulation described in Table VIII of U.S. Pat. No. 9,295,865, which is incorporated by reference, herein. In an optional embodiment the skin-hazard material is a presumed skin-hazard material.

Another embodiment is an effective method for decontaminating the outer integument of an animal without transferring contamination to the inner integument of the animal, the method comprising: providing a contaminated animal, wherein the contaminated animal has an outer integument comprising of either fur, hair, or feathers; wherein the animal has an inner integument comprising skin; and wherein a skin-hazard material is present on the outer integument; providing a first porous wetted wipe; using the first porous wetted wipe to sequester the skin-hazard material away from the contaminated animal by either wiping, blotting or rubbing the outer integument of the contaminated animal; not using free-flowing liquid in contact with the inner integument of the contaminated animal; and not promoting a liquid-phase transfer of the skin-hazard material from the outer integument to the inner integument. Non-limiting examples of a free-flowing liquid include those that move relative to the fur or outer integument, those that have shear or gravity induced macroscopic movement, those that can move under their own weight or those that have a sufficient volume to transport a liquid droplet the distance from hairs of animal fur down to the skin of the same animal.

In optional embodiments the method further comprises: not using free-flowing liquid in contact with the inner integument, wherein the free-flowing liquid comprises a mixture of soap and water; and not submersing any part of the contaminated animal in a liquid bath. Optionally further comprising: wherein, the skin-hazard material is a skin contact-hazard material, and effectively decontaminating the contaminated animal, wherein effectively decontaminating means reducing the presence of the skin-contact hazard material on the outer integument to a level below a contact-hazard level for the contaminated animal (for example, 5 mg of VX for a 25-kg dog, and while not transferring an amount of the skin contact-hazard material, which is above a contact-hazard level for the first species, from the outer integument to the inner integument. In further optional embodiments, the method further comprises: using a second wetted wipe to sequester at least a portion of the skin contact-hazard material away from the contaminated animal by either wiping, blotting or rubbing the outer integument of the contaminated animal; using the first wetted wipe to deposit a skin-hazard material solubilizing agent onto the outer integument; and using a second porous wetted wipe after using the first wetted wipe to sequester at least a portion of the skin-hazard material away from the contaminated animal by either wiping, blotting or rubbing the outer integument containing the skin-hazard material solubilizing agent, of the contaminated animal. In yet further optional embodiments the method also comprises trimming or cutting a portion of the outer integument off of the contaminated animal.

The patent of application file contains at least one drawing executed in color. Copies of this patent or patent application with color drawing(s) will be provided by the Office upon request and payment of the necessary fee.

BRIEF DESCRIPTION OF THE DRAWINGS

FIG. 7: Results of emulsification testing

FIG. 8: Results of Strat-M™ contaminated with MS and decontaminated.

FIG. 9: Results of Strat-M™ contaminated with CEPS and decontaminated.

FIG. 10: Results of German Shepherd fur contaminated with MS and decontaminated.

FIG. 11: Results of German Shepherd fur contaminated with CEPS and decontaminated.

DETAILED DESCRIPTION OF THE INVENTION

When an animal with hair, fur or feathers is exposed to a hazardous material, the hazard will often be deposited on the hair, fur or feathers (the outer integument). There is then a need to minimize the harm to the animal by removing the hazardous material, and also an opportunity to minimize the harm by preventing the hazardous material from being spread from the fur to the skin (the inner integument), recognizing that skin exposure presents an increased hazard due to absorption of the hazardous material into the body. Protecting military working dogs (MWDs) from exposure to hazardous chemicals and materials is especially challenging. The canine's fur is its first line of defense against less than immediately toxic exposures. The present invention provides a canine decontamination kit that can be used under field conditions, without additional logistical support. This means no additional water or equipment that is not part of the handler's standard operational kit. The canine decontamination kit provides the handler with a tool to save the life of the military working dog which has been exposed to chemical warfare agents (for example, HD and VX). This decontamination kit and procedures allows the handler to safely remove enough agent to keep the animal alive so the handler and dog can return from the field and then obtain additional decontamination and medical support.

The present invention teaches that the removal of chemical warfare agent simulants from canine fur is much easier than removal from surrogate skin membranes. The chemical simulant, and by extension the live chemical warfare agents, are capable of penetrating into the skin, while they do not appreciably absorb into the individual fur strands.

Decontamination utilizing a surfactant infused wet wipe to dissolve chemical simulants on the fur, followed by a dry wipe to absorb the solubilized chemical simulant and residual decontaminant yielded excellent decontamination performance. No fur to skin transfer was observed in these laboratory in-vitro samples. Averaging the removal performance across all simulants tested yielded 98.3+/−2.6% removal efficacy. This is an excellent performance for a decontamination method that could be used in the field with no additional logistical support.

Figure 1:
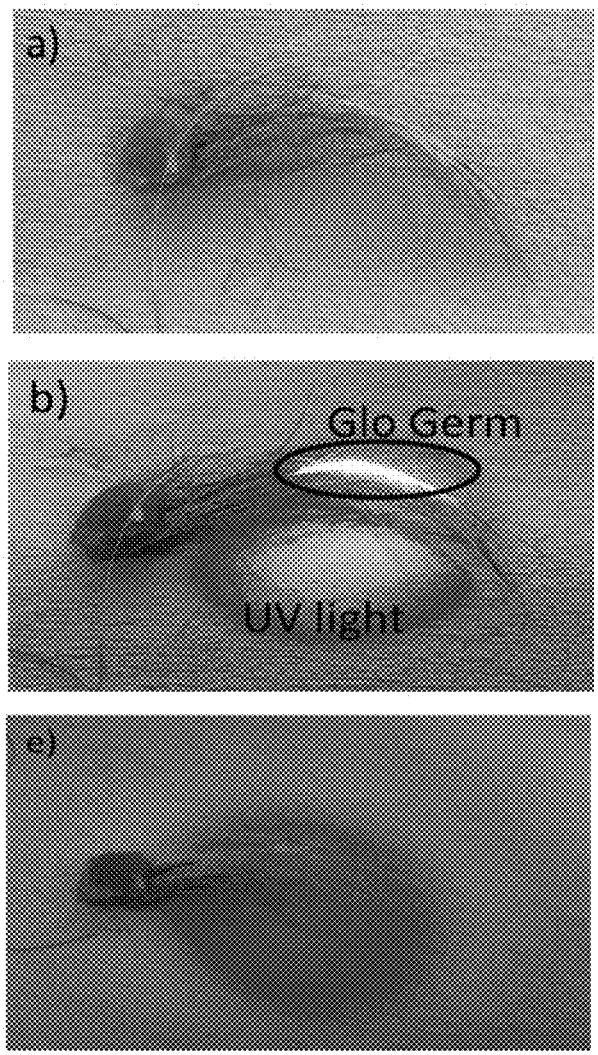
FIG. 1. German Shepherd fur plug, with Glo Germ® surrogate. a) image in visible, b) under UV light so that Glo Germ® fluoresces, e) image post decon under UV light shows complete removal of visible Glo Germ® surrogate.

FIG. 1 illustrates removal using a fluorescent surrogate for CW agent.

The decontamination approach for the present military working dog decontamination kit would enable a handler to treat a contaminated dog which has received over 58 times the lethal dose of chemical warfare agent on its fur, removing that contamination to below the $LD_{50}$ and saving the animals life so that it can return from the field to obtain additional medical logistical support.

The weight and size of the kit is small. The kit could weigh a little as 200 grams and be roughly the size of an ammunition pouch. This would ensure that it is small enough to not be a detriment to the canine handler, thus ensuring it would be available in a time of need.

Chemical warfare agents are particularly toxic and it is worth noting their toxicity to ensure an effective decontaminant is available, what it can successfully accomplish and how it can be safely implemented. The estimated mass of a small female Belgian Shepherd (an example of a potential military working dog breed) is 25 kg. The $LD_{50}$ percutaneous dose for VX is 0.2 mg/kg and for HD 60 mg/kg. Using the agent's density, it can be calculated that volume of liquid sufficient to kill 50% of the exposed animals is approximately 5 uL of VX and 1.2 ml of HD. Based on an average human mass of 75 kg, it only takes 15 uL of VX and 3.5 ml of HD to reach the handler's $LD_{50}$. These are very small quantities of chemical warfare agents. Realistic expectations and safety are paramount in the development of a handler operated kit for field operations.

The following terms are defined as to their meaning in the specification and in the accompanying claims.

The term "decon" is to be understood as meaning "decontamination".

The term animal means a live vertebrate having hair, fur, feathers, scales, horns or any structure comprising keratin on at least part of its body.

The term contaminated animal means an animal that has on its exterior a harmful, toxic, hazardous material or a material presumed to be harmful, toxic or hazardous, typically the materials is either a liquid or particulate solid. Non-limiting examples include chemical warfare agents, nerve agents, agents VX, GD, GB, blister agents, agent HD, toxic industrial chemicals, opioids, fentanyl, toxic industrial chemicals, toxic industrial materials, corrosive materials, and combinations thereof.

The term integument means an animal's protective layer. The integument is further defined in the present specification and in the accompanying claims as either the inner integument or the outer integument. The animal's outer integument contains structures extending out from the skin layer and may be fur, hair, or feathers. The animal's outer integument does not have a blood supply, and hazardous materials are not absorbed into the animal's circulatory system. The animal's inner integument is its skin, the thin layer of tissue forming the natural outer covering of the body of the animal. In certain embodiments of the present invention the animal may be a human and the outer integument is the human's hair. In no case should the animal integument to be decontaminated be interpreted to be claimed as an entire human organism.

The term wipe means a flexible piece of material, including paper, woven or nonwoven cloth, woven or nonwoven microfiber cloth, and flexible flat pieces of plastic. A porous wipe means a wipe that has the ability to absorb a liquid, where the liquid may be a skin-hazard material, or alternatively may be used to enhance cleaning. A dry wipe is used without added liquid. A wet wipe or a porous wet wipe contains liquid, where the liquid may be water, water with a detergent or surfactant, or a solvent with suitable properties, such as mineral oil or turpentine. When a liquid is used, it is added in limited quantity, so that the liquid remains on the wipe and is not readily transferred to the animal in an amount that promotes wicking, moving or liquid-phase transfer from the outer integument to the skin, or the inner integument. porous dry wipe means one or more flexible pieces of material, including paper, woven or nonwoven cloth, woven or nonwoven microfiber cloth, and flexible flat pieces of plastic. The porous dry wipe preferably has some internal porosity, which enables it to absorb and retain liquids. The ability to absorb and retain liquids is valuable in removing a liquid skin contact-hazard material.

The term wet wipe means a porous dry wipe as defined above to which a liquid has been added. The added liquid may be water, water with a detergent or surfactant, or a solvent with suitable properties, such as turpentine, glycerol, polyethylene glycol, propylene carbonate, ethanol, 2-propoanol, liquid hydrocarbons such as toluene or kerosene, mineral oil, vegetable oil, or ethyl acetate. When a liquid is used, it is added in limited quantity, so that when the wet wipe is applied to the outer integument the majority of the liquid remains on the wipe and the outer integument and is not readily transferred to the inner integument. The wet wipe preferably has some internal porosity, which enables the wet wipe to retain the added liquid.

When the liquid in the wet wipe is water plus a surfactant, the surfactant may be a nonionic, anionic, cationic or amphoteric surfactant. In one preferred embodiment, the surfactant is a nonionic surfactant. The surfactant solution may preferably be an aqueous solution containing linear, C12, secondary alcohol alkoxylate, polyoxyethylene (4) sorbitan monolaurate, octyldimethylamine oxide, and cocoamidopropyl dimethlamine oxide. For example, the surfactant solution is preferably a diluted (5% in water) solution of the surfactant formulation described in Table VIII of U.S. Pat. No. 9,295,865, which is incorporated by reference, herein.

The term liquid-phase transfer means transfer of the skin-hazard material from the outer integument to the inner integument by liquid, where the liquid dissolves or suspends the skin hazard material on the outer integument, allowing it to be transferred to the inner integument. The term liquid-phase transfer also means that solid particulates (such as fine opioid powder) is mechanically pushed or moved from the outer integument to the inner integument by the liquid (in non-limiting examples it may remain outside the liquid due to interfacial surface tension, or because it does not dissolve in the liquid or it does not dissolve in the liquid fast enough and doesn't have time to dissolve in the liquid or become entrained in the liquid as a solid-liquid slurry before it is moved by the liquid's surface pushing or moving it). The liquid-phase transfer can be accomplished by the liquid physically mobilizing the skin-contact hazard material, thereby effecting removal from a site on the outer integument and deposition at a site on the inner integument. The liquid-phase transfer can also be accomplished by the liquid dissolving the skin-contact hazard material from the outer integument and re-depositing the skin-contact hazard material on the inner integument, for example when the solvent evaporates. The liquid-phase transfer can also be accomplished by the liquid forming an emulsion or dispersion of the skin-contact hazard material, removing the skin-contact hazard material from the outer integument and re-depositing the skin-contact hazard material on the inner integument, for example when the emulsion or dispersion breaks down.

The term skin-hazard material means a material that can produce an undesirable effect when present on an animal's skin, where the undesirable effect can include toxic effects, a disease, an allergic reaction, and irritation. The term skin-hazard material also means a material that can cause harmful effects on an animal when in contact with the animal's skin, recognizing that the skin may be intact or may have a wound or other damage that allows hazardous materials to be more readily absorbed. The harmful effects of a skin-hazard material on intact skin can include poisoning, which can be fatal, and can also include blisters, rash, irritation, or allergic reaction. For chemical warfare agent HD, also called mustard agent (CAS number 505-60-2) the skin (dermal) contact hazard lethal dose in 50% of human subjects (the $LD_{50}$) is reported to be 100 mg/kg. For acrylonitrile (CAS 107-13-1) the dermal $LD_{50}$ (rabbit) is 63 mg/kg. For mercuric chloride (CAS 7487-94-7) the dermal $LD_{50}$ (rat) is 41 mg/kg. For sodium azide (CAS 26628-22-8) the dermal $LD_{50}$ (rabbit) is 20 mg/kg. The values above refer to hazards on exposure to intact skin. If there is an open wound, the material is much more readily absorbed, and there is a hazard both from chemical toxicants and from infectious material. For fentanyl (CAS 437-38-7), 3 mg is sufficient to kill an average adult human, so clearly a harmful amount could be absorbed through an open wound. Infectious materials, such as bacteria, fungi and viruses, can also enter the body and cause infection through an open wound. For example, anthrax spores are highly infectious; a value of 10,000 spores has been cited as a human $LD_{50}$, but a much smaller number of spores could be infectious. Further, skin-hazard material refers to a material that may contain hazardous substances, recognizing that is preferable to take the precautionary step of decontamination rather than conducting time-consuming tests to determine whether the suspected hazard is present.

For HD, using the above value of 100 mg/kg for skin contact hazard, and assuming a weight of 70 kg for a human, the dermal $LD_{50}$ is 7 g. No skin contact hazard value for HD on dogs is available, but assuming the same value as for humans of 100 mg/kg and a weight of 25 kg (55 lbs), the $LD_{50}$ is 2.5 g. An effective decontamination process should remove the hazard to well below the $LD_{50}$. For example, if a dog exposed to 5 g of HD (twice the $LD_{50}$) was treated with a decon procedure that removed 95% of the contamination and prevented it from reaching the dog's skin so that it could not be absorbed, then the dose that the dog received would be 0.25 g. At only 10% of the $LD_{50}$, this dose should not produce a lethal effect.

The term effectively decontaminating the animal means removing the skin-contact hazard material to a level that does not produce any undesirable effect should the skin-contact hazardous material move to or be transferred to the skin.

The term "decontaminate" means to treat a material or surface to mitigate the hazard presented by the material, or by the materials present on a surface.

The term "soap and water wash" means removing a contaminant from a surface by applying a mixture of soap and water to the surface, in a quantity such that the mixture of soap and water runs off of the surface. Ideally the contaminant is solubilized by the soap and water and removed as the excess soap and water mixture runs off.

The dry wipe can be used for wiping, blotting or rubbing.

The verb "rub", and its conjugated forms (i.e. rubbing), means to move one's hand or a cloth repeatedly back and forth on the surface of an item with firm pressure.

The verb "wipe", and its conjugated forms (i.e. wiping), means to clean or to dry an item by rubbing its surface with a flexible material.

The verb "blot", and its conjugated forms (i.e. blotting), means to dry a wet or a wetted surface by bringing an absorbent material in contact with the wet surface with minimal, trivial, or no lateral rubbing.

The present invention teaches the items for a kit that can be used under field conditions, without additional logistical support. This means using no additional water or equipment that is not part of the handler's standard operational kit. The canine decontamination kit provides the handler with a tool to save the life of the military working dog which has been exposed to chemical warfare agents (HD and VX). This decontamination kit and procedures allows the handler to safely remove enough agent in the field to keep the animal alive so the handler and dog can return from the field and then obtain additional decontamination and medical support, if needed.

Certain decontaminants are entirely inappropriate for dogs, such as any reactive or oxidizing chemicals, including bleach. Therefore, the present invention teaches decontaminant testing on non-reactive wipes and detergent based surfactants, soaps, shampoos, etc.

The ability of commonly used skin decontaminants to remove live nerve agent VX from a contaminated surrogate skin (Strat-M™ membrane) was evaluated, experiments conducted at a United States surety facility. The products evaluated include Dawn Ultra® (Procter & Gamble, Cincinnati, OH), SSDX-12® (TDA Research, Wheat Ridge, CO) and Reactive Skin Decontamination Lotion (RSDL®) (Emergent BioSolutions, Gaithersburg, MD). VX is a highly potent nerve agent with an $LD_{50}$ of 7 ug/Kg.

For each test, a Strat-M membrane was contaminated with 2 uL nerve agent VX and allowed to age, covered, for 30 min. Following the aging period, 20 mL of Dawn Ultra or SSDX-12® solution was added to submerge the contaminated membrane for 10-minutes. For the RSDL sample, the lotion contents of one towelette packet, approximately 5 grams of RSDL lotion was added for 10 minutes. After the 10-minute residence time, each sample was submerged into 20 mL of deionized water for an additional 10 minutes followed by an extraction in 10 mL of acetone. To ensure complete extraction of all residual agent, all samples were sonicated for 10 minutes prior to being sampled for analysis.

The average untreated control recovery of VX was 1937 ug or 96% of the applied mass. The sample treated with SSDX-12® recovered an average of 50.2 ug or 2% of the applied mass. The sample treated with Dawn Ultra recovered an average of 73.1 ug or 4% of the applied mass. The sample treated with RSDL recovered an average of 121.1 ug or 6% of the applied mass. The residual VX after treatment with SSDX-12 was statically less VX compared to RSDL (t-stat=2.41e-5) and less than Dawn Ultra (t-stat=0.00195). These results confirm that SSDX-12® is more effective in removing a chemical warfare agent from a skin surrogate than alternative decon materials, including a commonly used detergent. Thus, SSDX-12® is a preferred embodiment of the present invention when used in the decontamination of animals.

Figure 2:
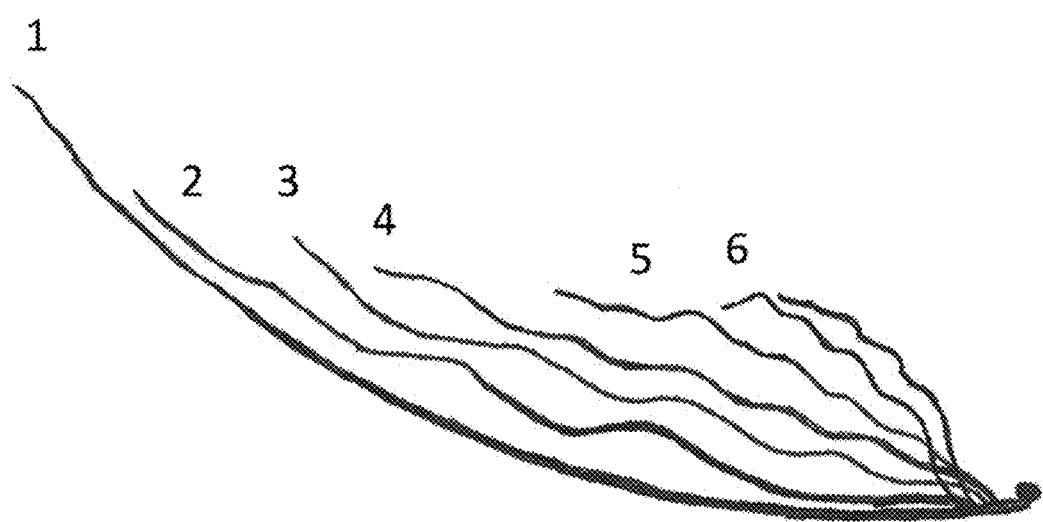
FIG. 2: Diagram of six types of hairs for the dog.

Canine Hair Composition and Analysis: Dogs have six types of hairs, which organize themselves into hair bundles (FIG. 2). The strongest and longest of these is the Straight Hair, which is also called the guard hair and is classified as a protective hair (number 1 in FIG. 2). The remaining are named (in order of diminishing size and firmness) Bristle Hairs, Wavy Bristle Hairs, Bristled Wavy Hair, Large Wavy Hair, and Fine Wavy Hair. The first two of these (numbers 2 and 3) are classified with the Straight Hairs as protective hairs. The last 3 hairs comprise the undercoat with Bristled Wavy (number 4) being the largest. For the purpose of this disclosure and accompanying claims, all hair is part of the "outer integument".

German Shepherds have ~100-300 hair bundles/$cm^2$. Assuming an average of 7 hairs/bundle and a body region with 100 bundles/$cm^2$, about 700 hairs/$cm^2$ would be predicted. Hairs were counted from three plugs from the back of the study dog, and contained 541, 743 and 603 hairs for a mean of 629. This equates to about 6.3 hairs per bundle and agrees well with the above approximation. Hairs were also counted from three plugs from the thigh of the study dog, and they contained 1072, 1341 and 1044 hairs for a mean of 1152, which would equate to 11.5 hairs per bundle suggesting variation in hair density based on anatomic region.

Canine Wicking Experiments: For the wicking studies, back and thigh skin samples were collected from a German Shepherd donor dog that had been euthanized for health-related reasons. The skin with hair was frozen to −80° C. and then freeze-dried. The freeze-dried skin was cut into 1 $cm^2$ plugs for dipping of hair into chemical agent simulants, to determine the degree to which different chemicals wicked up the hair. The thigh hair plugs visually appeared denser and had a fine brush-like appearance, where hair plugs from the back region appeared to have longer and more coarse looking hairs that were less dense at their distal ends.

Figure 3:
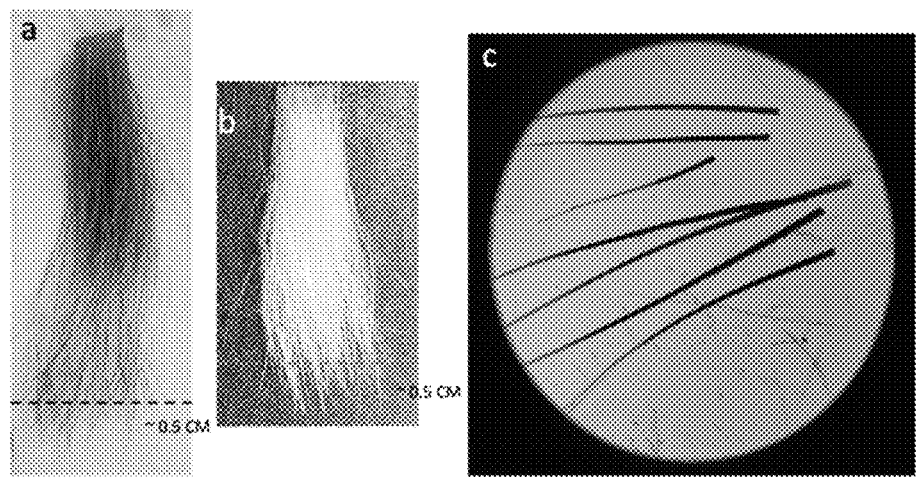
FIG. 3: (left) photograph of fur plug from back (center) photograph of fur plug from thigh, (right) microscope photograph of the hair.

Three representative hair plugs were selected from the back and thigh. Using a metric ruler and a magnifying glass, the hair from each plug was cut at 0.5 cm as shown in FIG. 3 (left canine back fur) and right image for thigh fur, to ascertain the types of hairs that would be exposed to the chemicals during dipping to 0.5 cm. Clipped hairs from both body regions were placed in a culture dish and examined at 40× with an Olympus inverted microscope (see the right image in FIG. 3). The hair tips from both regions across 3 plugs/region were determined to be exclusively Straight and Bristle Hairs, representative of the protective coat of the dog.

Hair plugs (N=3) were dipped in simulant chemicals as described above (2 second duration, 0.5 cm depth) for a total of 27 hair plugs/hair region/simulant. Briefly, 3 plugs were attached to a suspension bar and lowered into empty beakers to confirm that each plug was in contact with the bottom of the beaker and if not, adjusted so that it did. A level was also used to confirm that the contact across the 3 beakers was uniform. Once this calibration procedure was finished, the 3 empty beakers were replaced with 3 identical beakers containing the simulant filled to a depth of 0.5 cm. The plugs were lowered in to the beakers until the longest hairs were in contact with the bottom of the beakers. After a 2 second contact time, the suspension bar was raised and transferred to a $2^{nd}$ fabricated device and suspended above conical centrifuge tubes. The bar height was pre-adjusted so that 1 cm of the hair was suspended in each tube. One-centimeter lengths of the hair were cut into pre-labeled tubes at 30 seconds. This procedure was repeated twice more with 1 cm hair sections cut at 5 and 10 minutes. This procedure was then repeated with new plugs for 2 cm and 3 cm clippings, at 5 and 10 minutes, respectively. Tubes were coded and labeled with 3 numbers and a letter as follows: 3-1-1-B indicating simulant 3, 1 cm hair length cut, shortest (30 second) waiting time prior to cutting, and the sample was from the back of the dog.

Hair plugs were dipped in Glo Germ® (oil or lotion) to 0.5 cm depth to visually determine how this agent would wick up the hair at 30 seconds, 5 minutes and 10 minutes post dipping. Based on our previous detailed analysis of the hair plugs, this depth was expected to contact primarily the protective Straight and Bristle Hairs. The Glo Germ® oil fluoresces an orange color under a UV lamp. The Glo Germ® lotion fluoresces a blue color under a UV lamp. Visually, the Glo Germ® oil did not move upward on the dipped hairs at all over the entire 10-minute period.

Glo Germ® oil values wicking distances did not significantly change from 30 sec to 10 minutes. The back hairs tended to have more angle to them, while the thigh hairs appeared denser with a flared pattern. The Glo Germ® lotion, wicking measurements were comparable to the Glo Germ® oil measurements and like the Glo Germ® oil, did not significantly change over time.

The Glo Germ® experimental trials revealed that both the oil and lotion-based liquid mediums had minimal wicking capability when suspended in a vertical position to the ground.

Additional tests used methyl salicylate (MS) and 2-chloroethyl phenyl sulfide (CEPS), which are accepted surrogates for the physical properties of CW agents, particularly HD. The results of tests with those chemical agent simulants are described below.

Methyl salicylate (MS) is a volatile liquid. The chemical analysis suggests that the MS on the hair tips evaporated over time. In 4 of 5 cases, the mass of MS was greatest on hair tips clipped at 30 seconds. MS mass tended to diminished with time, with 4 of the 6 samples containing non-detectable MS at 10 minutes.

Hair plugs from the thigh region contained significantly more hairs than plugs from the back region. Mean mass of MS on hair samples at 30 seconds, 5 minutes and 10 minutes were (mg): Back: 0.195, 0.029, 0.000; Thigh: 0.170, 0.129, 0.042. The data suggest a slower evaporation rate from the lateral thigh region where hair density is greater.

2-chloroethylphenylsulfide (CEPS) had similar results to both the MS and Glo-germ results. It was seen that the thigh hair, with its increased number of hairs, picked up significantly more CEPS than the back-fur samples.

Wicking rate experiments demonstrated that CEPS and MS do not wet or wick on canine fur.

Figure 4:
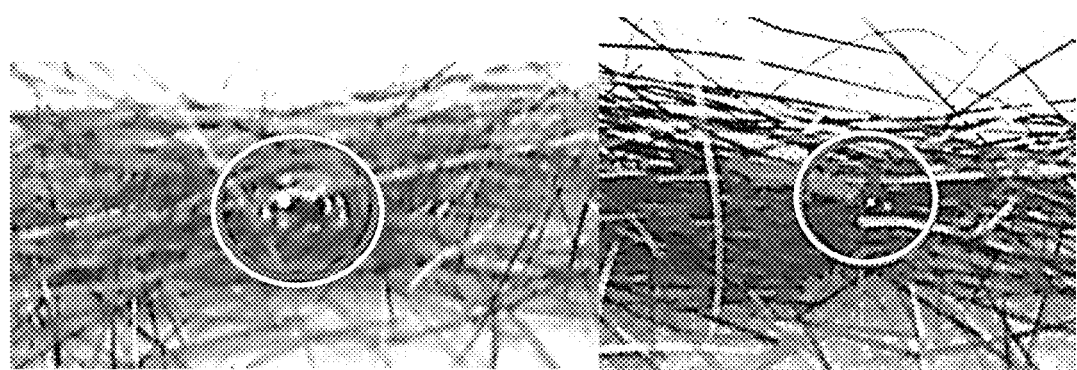
FIG. 4: (left) a droplet of methyl salicylate (MS) on dog fur, (right) same sample of MS on dog fur after hour.

To evaluate the fur wicking of these simulants, tests were conducted to demonstrate just how well German Shepherd canine fur resists wetting by the MS simulant. For this test, loose German Shepherd fur was clumped into a pile and a small droplet of simulant was added to see how long a sessile droplet would last on the fur. Photographs of that test are shown below in FIG. 4. As can be seen, the droplet does not wick into the fur and remains on the fur even after an hour. Based on these simulant experiments chemical warfare agents will not quickly wick up a canine's fur and the primary decontamination challenge will be finding a way to remove the agent from the fur without transferring it to the skin.

Figure 5:
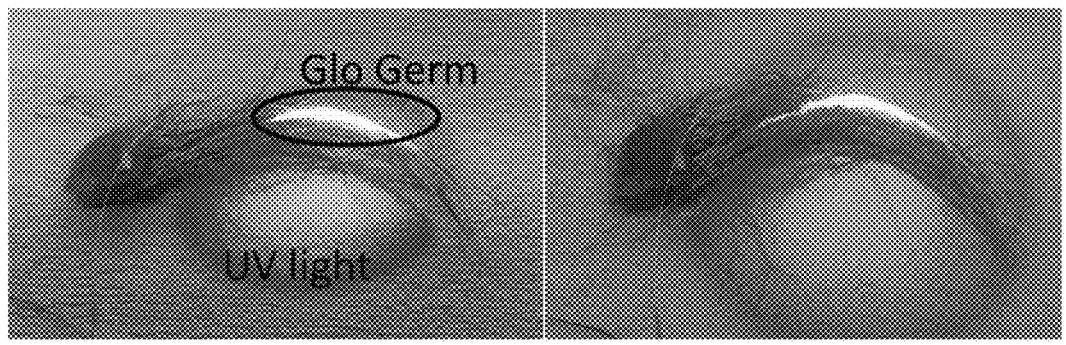
FIG. 5: (left) Orange mineral oil Glo Germ® on a fur skin plug, (right) same sample after 30 minutes.
Figure 6:
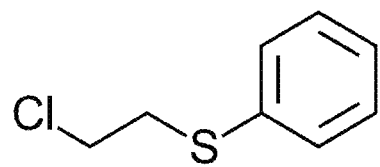
FIG. 6: Structures of chemical HD simulants.
Figure 6:
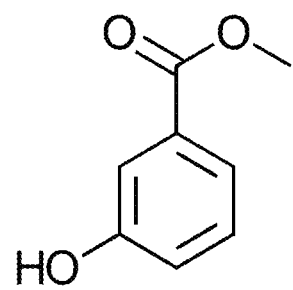

Verification tests using orange mineral oil Glo Germ® were also conducted, photographs are shown in FIG. 5. Here, after 30 minutes there appears some slight wicking into the fur, however it is slow. This suggests that mineral oil Glo Germ® could be a representative chemical warfare simulant if used in the correct quantities. These results are consistent with the dip tests described above.

Based on our experiments taught here, canine fur does not wick chemical agent simulants up its fur. The agents do not wet or wick the hair. Based on these results, military working dogs that are well groomed and brushed/combed so that its fur is not matted have an excellent temporary protection to chemical warfare agents. Unless the agent is somehow pushed through the fur or comes in contact with a region of the body that does not have fur, the individual hair will keep the agent of the animal's skin. Proper decontaminant selection and decontamination technique will be important in removing the agent from the fur without transferring it to the skin of the dog. Techniques that utilize large quantities of soap and water may actually negate the dogs' natural protective fur barrier as the surfactant wetting agent will dissolve the agent and wet the fur providing a path of the agent to penetrate to the skin. The present invention teaches that proper decontamination should involve adequate removal of the agent from the fur prior to a thorough wash of the dog. This is in direct contrast to the prior art, which teaches the required use of copious amounts of water or a water bath.

Preliminary Decontamination Testing/Chemical emulsification and reactive testing: SSDX-12®, a dual-purpose cleaner and decontaminant, or any surfactant used to remove chemical agents must be capable of solubilizing the agent. One of the keys for a successful decontamination is ensuring the surfactant can solubilize the chemical for long enough that it can be removed. If an unstable emulsion if formed, the agent will simply crash out of solution. This can lead to smearing and an increase in the surface area the agent contacts. For a MWD whose fur is contaminated by a CW agent, this increase in surface area in contact with agent translates to an increase in skin contact and greater chemical dose for the dog.

An emulsification test was performed with the simulants (methyl salicylate (MS), chloroethyl phenyl sulfide (CEPS), and orange mineral oil based Glo Germ® and the decontaminants Mane 'n Tail Shampoo, Mane 'n Tail Conditioner, Chlorhexidine solution, Hibiclens, Dawn dishwashing detergent, Palmolive dishwashing detergent, and SSDX-12®. Testing involves combining the two in a sample vial and then agitating them to allow adequate mixing. The samples were then evaluated at set times to determine when the emulsion separates and the simulants fall out of the decon solution. The longer the time required for the simulant to crash out, the more stable the emulsion.

The decontaminants were diluted 1 part decontaminant to 30 parts water; Hibiclens was tested at this dilution and also undiluted. The simulant was combined with the decontaminant at a ratio of 50-parts decontaminant and 1-part simulant.

The results are shown in FIG. 7; in columns 3 and 4, longer times indicate the production of a more stable emulsion and thus represent a potentially better ability to dissolve and remove the simulants. Ultimate decontamination performance will also depend on the surface and how well the agent interacts with that surface. Mane 'n Tail® shampoo worked better with the chemical simulants than with the Glo Germ®. The Mane 'n Tail® conditioner was much better with the Glo Germ® but very poor at solubilizing the chemicals. Mane 'n Tail® pet shampoo contains water, sodium lauryl sulfate, cocamidopropyl betaine, cocamide MEA, glycol distearate, sodium chloride, propylene glycol, fragrance, hydrolyzed collagen, citric acid, dmdm hydantoin or methylchloroisothiazolinone/methylisothiazolinone. Mane 'n Tail Conditioner contains Water, Distearyldimonium Chloride, Stearyl Alcohol, Stearamidopropyl Dimethylamine Lactate, Cetyl Alcohol, *Cocos nucifera* (Coconut) Oil, Glycerin, Cetearyl Alcohol, Phenoxyethanol, Fragrance, *Glycine soja* (Soybean) Oil, Polysorbate 60, Steareth-20, Methylparaben, Sodium Chloride, PEG-150 Stearate, Hydrolyzed Collagen, Propylparaben, Lanolin, *Olea Europaea* (Olive) Fruit Oil, Yellow #5 (CI 19140), Benzyl Benzoate, Citronellol, Geraniol, Hexyl Cinnamal, Butylphenyl Methylpropional, Limonene, Linalool, and Alpha-isomethyl Ionone.

Chlorohexidine performance was 1 minute or less with all simulants, which was expected as this product did not appear to contain surfactants which would have helped solubilized these simulants.

Hibiclens® is a skin cleanser with 4% w/v chlorohexidine gluconate as a disinfectant; other ingredients include fragrance, gluconolactone, isopropyl alcohol 4% w/v, lauramine oxide, poloxamer 237, purified water and red 40. Hibiclens® is effective when used neat at a 50:1 ratio with the simulant providing a stable emulsion for >4 hrs, 11:30 min and 10 min for Glo Germ®, CEPS and MS respectively. We increased the concentration of simulants to 50:5 and found that the entire solution gelled and solidified.

Dish soaps Dawn® and Palmolive® were not very good at emulsifying chemical simulants, with emulsion stability of 1 minute or less with both CEPS and MS, compared to SSDX with a stability of >2 minutes with CEPS and >4 minutes with MS.

SSDX-12® formed a better emulsion with the simulant than the dish soaps and all of the other cleaners with the exception of Hibiclens® (which must be used at the right dilution and without excessive agent or it will form unwanted gels and solid particles).

No decontaminants were excluded based on these test results. We carried them forward to the skin and fur testing.

In these tests a skin surrogate was used to identify what products are good at removing toxic compounds from skin. Strat-M™ (Merck Millipore) membranes are synthetic, non-animal-based models used to evaluate transdermal diffusion; they are used as a human skin surrogate to study diffusion of pharmaceuticals, cosmetics, pesticides and chemicals. While these membranes are designed to mimic human skin, they are particularly useful because they make it possible to run tests with minimal variability. We inoculated 25 mm diameter (~1 inch) Strat-M™ membranes with 10 uL simulant chemical agents (MS and CEPS in separate tests), waited 30 minutes, and then conducted decontamination tests using the same decontaminants. The decontaminant was applied and allowed to dwell for 10 minutes, then submerged in DI water for 10 min to wash away the decontaminant. The membrane was then extracted with acetone. The simulant extracted from the membrane (that is, simulant that permeated into the membrane, so that it could not be washed away) was quantified using GC-MS. Three separate replicates were conducted for each test simulant-decon pair.

Three control experiments were conducted for both simulants (MS and CEPS). First, directly added the simulant to acetone to verify proper application mass (ensuring our application and quantification masses agreed). Of the 10 uL applied we directly recovered 102.1% of the MS and 102.4% of the CEPS. Second, we contaminated a Srat-M membrane and then directly recovered the sample with acetone to ensure the simulant could be recovered. We recovered 95.4% of the MS and 97.0% of the CEPS. The final control test was the use of water as a decontaminant to determine the benefit of any decontaminant, those results are provided with each experimental series and present below.

The decontamination results for membranes that were contaminated with MS are shown in FIG. 8. The first result to note is the water only decontaminant which showed 14.1% removal of MS. MS has a greater water solubility that CEPS, so we would expect the MS water decon to be better than CEPS. Unfortunately, the other decontaminants were only marginally better than water and provided a statistically equivalent performance. Mane 'n tail conditioner was the poorest performer.

We suspect the reason for the uniform poor performance of the decontaminants is that most of the MS is penetrating into the membrane too far to be recoverable during the decontamination process and that the surfactants in the decontaminant cannot reach the contaminant. The MS remaining on the surface is easily removed. To gain additional granularity to the different decontaminants, it may be necessary to shorten the contaminant dwell time on the membrane. Unfortunately, there was no time to run these additional tests.

The decontamination results for the membranes that were contaminated with CEPS are shown in FIG. 9. The first result to note is that the water only decontaminant showed only 1.99% removal of CEPS. All of the other decontaminants showed improvement compared to the water control. The best performers (Palmolive®, Dawn® and SSDX-12®) were statistically matched, as determined by a two-sample t-test. Mane 'n tail conditioner was again the poorest performer.

Canine hair decontamination testing: In this example, we are quantifying the removal of simulants (MS and CEPS) from a canine fur sample. We used a fixed mass (~0.05 grams) of German Shepherd dog fur inoculated fur samples with 10 uL of simulant chemical agents; we waited 30 minutes then conducted decontamination. The decontaminant was applied and allowed to dwell for 10 minutes. The fur was then extracted with acetone, which was analyzed with GC-MS and quantified.

The decontamination results for German Shepherd fur that was contaminated with MS are shown in FIG. 10. The first result to note is that water-only decontaminant showed 79.9% removal of MS. Again, MS has a greater water solubility that CEPS, so we would expect the MS water decon to be better than CEPS. Fortunately, it appears the MS simply does not penetrate into the fur very well and the decontaminants were able to remove significant amounts of the chemical from the fur.

The best performing decontaminants were the SSDX-12®, Dawn® and Mane 'n Tail® shampoo. The worst performing was the Mane 'n Tail® conditioner. The neat Hibiclens® samples, which had shown some promise with the skin decon, appeared to form a gel during this testing and could not be removed from the German Shepherd hair for analysis. Those samples ended up being discarded.

The decontamination results for the German Shepherd fur that were contaminated with CEPS are shown in FIG. 11. The first result to note is that the water-only decontaminant showed only 25.4% removal of CEPS, significantly less than the more water-soluble MS.

Combined canine fur and skin surrogate decontamination testing: Our decontamination testing of separate canine fur and skin simulant showed that if the simulants reach the skin, they penetrate into it readily and are then very difficult to adequately remove. We are further teaching that the simulants do not appear to penetrate into German Shepherd fur, enabling relatively easy removal.

In this task, we evaluated the decontamination performance of a simulated canine pelt where German Shepherd fur was placed onto a simulant skin membrane (Strat-M™ membrane). The overlying fur is then contaminated with 10 uL simulant chemical agents (MS and CEPS in separate tests), allowed to dwell for 30 minutes, and then decontamination tests using the same decontaminants as previous tests were conducted.

The decontaminants were Mane 'n Tail Shampoo, Mane 'n Tail® Conditioner, Chlorhexidine solution, Hibiclens®, Dawn® dishwashing detergent, Palmolive® dishwashing detergent, and SSDX-12®; water only was used as a decontaminant control. The decontaminant was applied and allowed to dwell for 10 minutes; the sample was then submerged in DI water for 10 min to wash away the decontaminant. The membrane and fur were then extracted separately with acetone. The simulant extracted from the membrane and fur were quantified individually using GC-MS. Three separate replicates were conducted for each test simulant-decon pair.

This test allows us to get insight into how well the simulant penetrates though the canine fur. It also allows us to look at what happens during decontamination, the goal is to lift the simulant from the fur while preventing its deposition and penetration into the skin from the decon solution. To establish good performance, we looked for a decontaminant that leaves minimal simulant on the fur and skin.

Figure 12:
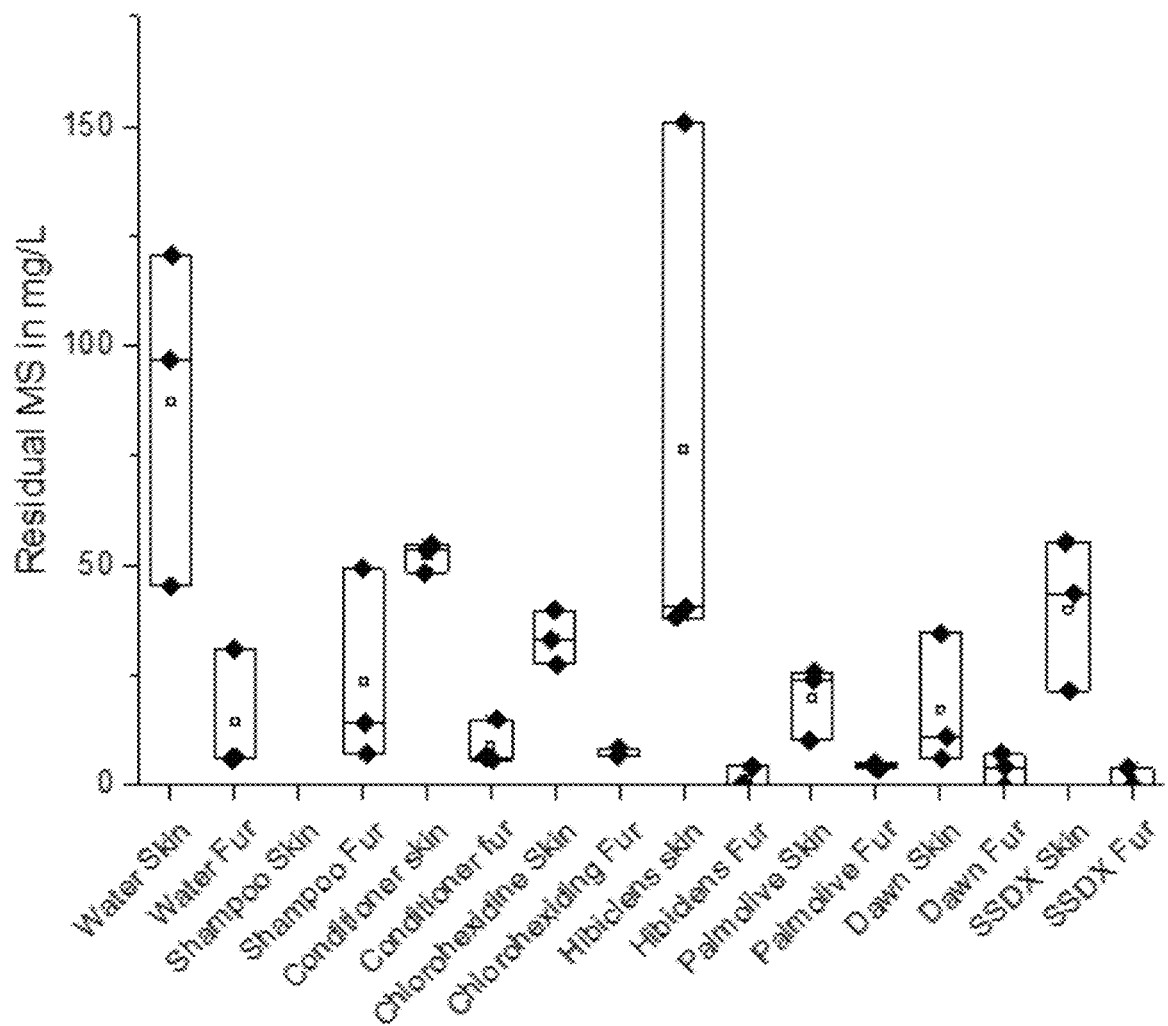
FIG. 12: Decontamination of MS from skin-simulant samples

The decontamination results for MS contaminated samples are shown in FIG. 12. Control experiments using water only demonstrated about 56% decontamination. It also suffered significant transfer of MS to the skin, with 6.2% of the starting challenge being found in the skin. Similar results were seen with the shampoo and Hibiclens®. The surfactant products SSDX®, Dawn® and Palmolive® were statistically matched in removal performance from fur and skin and achieved the greatest combined removal of MS from both the fur and skin, removing between 91.2 and 95.5% of the applied simulant.

Figure 13:
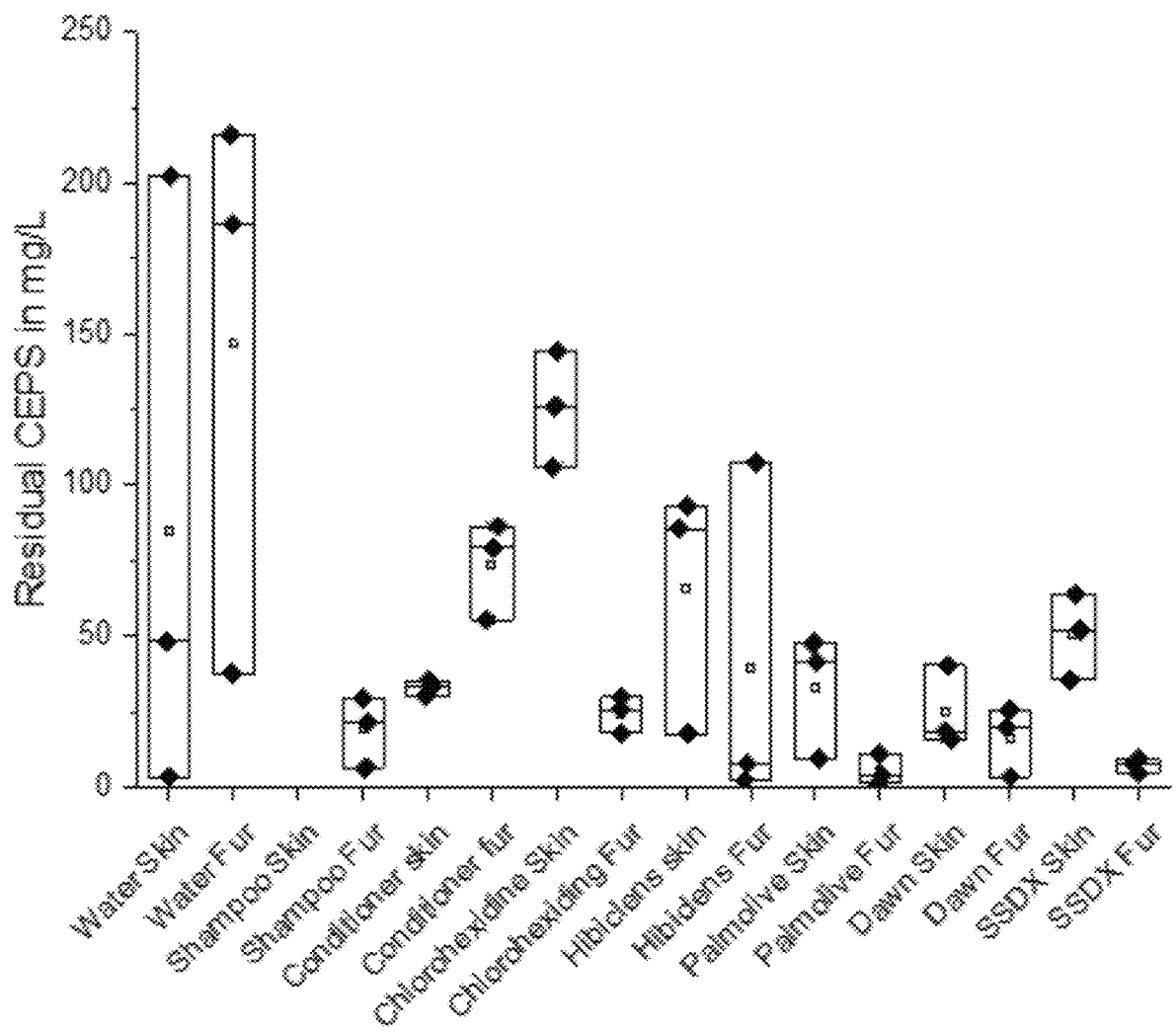
FIG. 13: Decontamination of CEPS from skin-simulant samples

The decontamination results for the more hydrophobic CEPS contaminated samples are shown in FIG. 13. Control experiments using water only performed very poorly with only 20% decon, removing little from the fur and transferring significant amounts to the skin, with 36% of the starting challenge being found in the skin. The shampoo was reasonably good at removing the CEPS from the fur however, with about 90% decon; however, much of it (43% of the starting challenge) was transferred to the skin. Chlorohexidine solution and Hibiclens® skin cleanser also suffered from transfer from the fur to the skin during decontamination with the skin having a greater average simulant residual than the fur.

The best performing products were again the surfactant solutions of SSDX®, Dawn® and Palmolive® which provided a statistically matched removal performance from fur and skin and achieved the greatest combined removal of CEPS from both the fur and skin, removing between 87.74 and 91.85% of the applied simulant. In live agent tests, SSDX-12® provided the highest (statistically significant) agent VX removal from a skin surrogate membrane, thus the present invention teaches this as the preferred embodiment.

Next, we set out to take the knowledge obtained using the non-agitated decontamination solutions from the previous tasks and pull it together to try a wipe decontamination method. The objective is to wipe away the droplets of contaminant that are beaded up on the surface of the fur without allowing them to reach the skin. Dawn detergent contains C10-16 alkyldimethylamine oxide, C9-11 pareth-8, PEG-14 PEG-24/PPG-16 copolymer, phenoxyethanol, sodium chloride, sodium hydroxide, sodium laureth sulfate, sodium lauryl sulfate, styrene/acrylates copolymer, denatured ethyl alcohol, colorants, fragrances and the preservative methylisothiazolinone. In separate experiments, it was shown that SSDX-12® performed better than Dawn® detergent in removing a chemical warfare agent VX.

In this next example, canine fur skin plugs were contaminated with 10 uL of simulant (mineral oil-based orange Glo Germ®, CEPS and MS) and the simulants were allowed to sit for 30 minutes. A commercial, disposable shop paper towel was then wetted with 30:1 diluted SSDX-12® and used to wipe the canine fur sample. This wet wipe was followed by wiping with a dry disposable shop paper towel to absorb any decon solution and the solubilized simulant. The fur was then separated from the skin and both the fur and skin were extracted separately using acetone. Quantification using GC-MS was performed using calibration curves. Glo Germ® testing provided a simple, qualitative visual analysis.

Figure 14:
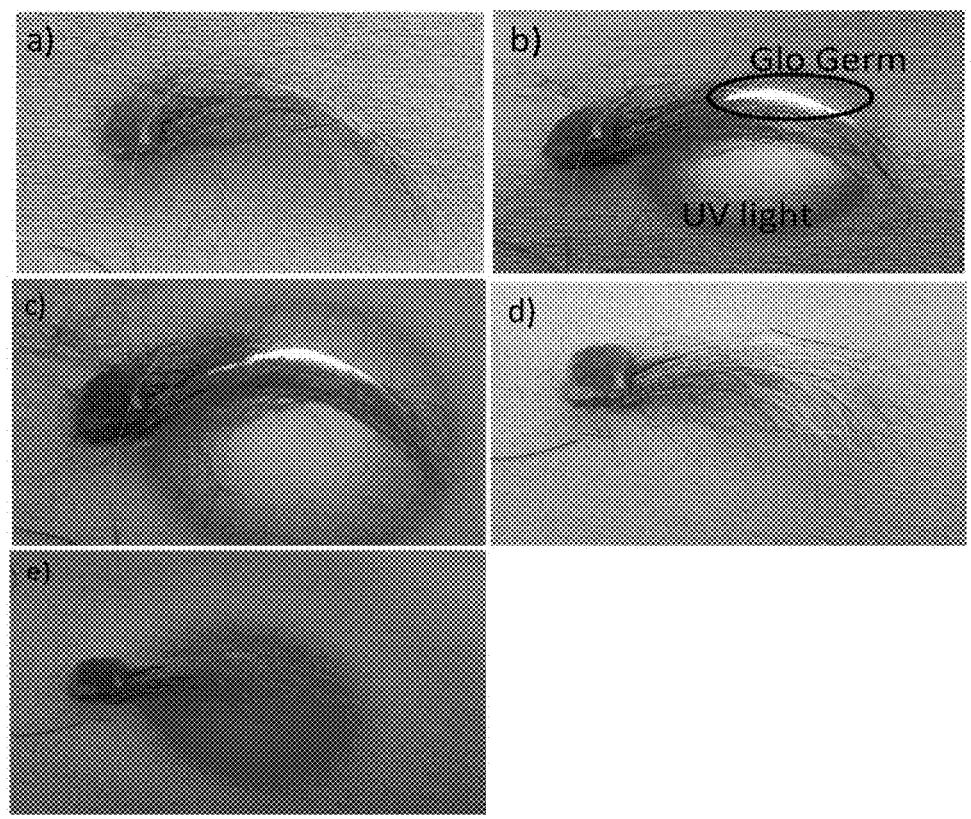
FIG. 14: Glo Germ® wipe decon experiment photograph a) visible light image of fur plug contaminated with Glo Germ®, b) fur plug under UV-light designed to make Glo Germ® glow, c) 30 minutes after inoculation, d) visible light image post decon, e) UV-light image post decon.

For the initial qualitative Glo Germ® test, a canine fur plug was taken and 10 uL of Glo Germ® oil was added. A series of photographs of the experiment is shown in FIG. 14. Photograph a and b show the initial contaminated canine fur plug with image A being in visible light showing the orange material and image B under a UV flashlight which causes the Glo Germ® to fluoresce. Photograph C shows the UV illuminated sample 30 minutes after inoculation, very little if any wicking of the simulant up the hair is observed. The sample was then decontaminated using a wet wipe with 30:1 diluted SSDX-12®. Image D is a photograph of the fur plug in visible light afterwards, Glo Germ® is not obviously present. In image E, under UV light, there is no obvious Glo Germ® present. Further, there is no obvious florescence on the skin which would be indicative of transfer during decontamination. Again, Glo Germ® tests are only qualitative, but the removal does show promise.

Wipe decontamination testing was also conducted with MS and CEPS contamination. Testing was conducted as previously described; three skin/fur plug sample were evaluated for each simulant. The fur and skin were extracted separately and quantified to determine if any transfer had taken place.

Decontamination results for MS contaminated fur plugs showed no detectable MS on the skin samples demonstrating at no MS was transferred to the skin during the decon procedure. Further, only one of the three fur samples tested detected MS while no remaining MS was detected on the other two samples. The average decontamination efficacy of MS from the fur was 99.1+/−1.6%.

Wipe Decontamination results for CEPS contaminated fur plugs showed no detectable CEPS on the skin samples demonstrating at no CEPS was transferred to the skin during the wiping decon procedure. Further, two of the three fur samples tested detected CEPS while no remaining CEPS was detected on the other sample. The average decontamination efficacy of CEPS from the fur was 97.6+/−3.8%.

The results of this wipe decontamination testing which utilized a single wet wipe with a dilute 30:1 solution of SSDX-12® followed by a dry wipe to remove the dissolved agent showed excellent performance. This technique was certainly more successful than the test utilizing large aliquots of decontaminant solution as described above in the previous tasks.

Test with dog fur on skin: Tests of decontamination procedures were carried out using 3-inch by 3-inch samples of dog fur on skin, which was contaminated with nine 10-microliter drops (total 90 microliters) of 2-chloroethyl phenyl sulfide (CEPS), a surrogate for the chemical warfare agent HD (sulfur mustard). After allowing the CEPS to reside on the fur for 30 minutes, it was removed by combinations of dry and wet wipes. The dry wipe was a microfiber towel, dimensions 8 inches by 8 inches. The wet wipe was the same towel wetted with a 3.2% solution of detergent SSDX-12® in water. The detergent solution was added to the wipe, and the solution was then removed by squeezing it out so that the wet wipe did not drip. The liquid loading was approximately 0.2 g per square inch.

After each test, the fur and the skin were separated. Each sample was then extracted with solvent and the solvent extract was analyzed by gas chromatography-mass spectrometry (GC-MS) to determine the amount of CEPS present in the sample. Controls without any decon procedure determined that essentially 100% of the applied CEPS could be detected in the extracts. Our goals were first, to show that CEPS has been removed from the fur, and second, to show that no CEPS had reached the skin during the decon procedure.

In one test, wet and dry wipes were randomly scrubbed back and forth with hand pressure over the 3-inch by 3-inch sample. Analysis showed 74.5% overall removal, but 2.5% of the challenge was transferred to the skin.

In another test, the wipe was moved over the 3-inch by 3-inch sample against the direction of fur growth. Light pressure was used so as not to press the fur against the skin. Three wipes were used in separate steps. The first wipe procedure used a dry wipe, the second wipe procedure used a wet wipe, and the third procedure used a dry wipe. Analysis showed 97.1% overall removal and no detectable amount of CEPS transferred to the skin. This result showed that the wipe procedure can effectively remove a liquid contaminant from fur without transferring it to the skin.

In this constructive reduction to practice example (no live animal testing was conducted, results are extrapolated from tests on pelts) the contaminated animal is a German shepherd working dog that has been exposed to a highly toxic liquid. The event leading to the contamination was the detonation of a terrorist device containing the chemical warfare agent sulfur mustard (SM, also called agent HD). The device produced an aerosol cloud of liquid agent droplets that contaminated everything in the area. The dog was contaminated by the aerosol droplets, and also by brushing against contaminated objects. The contamination was deposited on the dog's fur (the outer integument). While the liquid is extremely toxic, we have discovered that the liquid on the dog's fur essentially remains where it was deposited and does not wick to the skin (the inner integument). On the fur the toxic liquid is not absorbed into the dog's body because there is no blood circulation in the fur. On the skin the liquid is absorbed into the dog's body; it is a skin-hazard material, also referred to as a contact hazard. Skin exposure, on dogs and in humans, can be harmful and even fatal. Therefore, it is critical to remove the liquid from the dog's fur while preventing transfer to the dog's skin.

In a first step, the dog is wiped with a porous dry wipe of dimensions 16 inches by 16 inches that is applied to all of the contaminated area, rubbing against the direction of hair growth. In a second step, the dog is wiped with a porous wet wipe of the same dimensions that is applied to all of the contaminated area, rubbing against the direction of hair growth. The porous wet wipe is wetted with a solution of a 30:1 dilution of SSDX-12® in water with an amount up to the point where the wet wipe does not drip In an embodiment, 50 grams of 30:1 dilution SSDX-12® is applied on a 16×16 microfiber wipe is appropriate. In a third step, the dog is wiped with a porous dry wipe of the same dimensions that is applied to all of the contaminated area, rubbing against the direction of hair growth. The combination of these steps has been shown to remove more than 97% of the liquid while not transferring any of the liquid to the skin.

The above methods for decontaminating outer integument should also be understood to be effective on other animals besides dogs, including birds as well as mammals. For the purpose of the methods taught in this present disclosure the animals including horses, cattle, buffalo, sheep, goats, cats, bears, camels, otters, seals, antelope, llamas, apes, kangaroos, giraffes, chickens, turkeys, ducks, geese, eagles, doves, gulls, parrots, jays and penguins, are functional equivalents of dogs, when the functional equivalent animals have an inner integument and an outer integument as defined above.

An advantage of the procedure in this example compared to washing with soap and water is that washing with soap and water can cause liquid-phase transfer, transferring the liquid agent to the skin, where is can harm the contaminated animal. A further advantage is that the dry and wet wipes are very low mass and volume. The three wipes of this example would weigh less than 6 ounces and fit in a pouch of dimensions 6 inches by 7 inches by 2 inches. In contrast, washing with soap and water would require at least 20 gallons of water, weighing at least 160 pounds. Yet another advantage is that when a soap and water wash is used on a dog, the dog will tend to shake to dry itself, and the shaking can spread the contaminated wash water to the handler and the surroundings. This problem is avoided when removing the skin-hazard material with wipes. Still another advantage is that the contaminated wipes can be easily contained in a small pouch for disposal. In contrast, the contaminated water from soap and water wash is a significant challenge for disposal. Yet a further advantage is that the wipes are easily used by a handler wearing personal protective equipment, for example chemical-resistant gloves.

Although the present invention has been described in considerable detail with reference to certain preferred versions thereof, other versions are possible. Therefore, the spirit and scope of the appended claims should not be limited to the description of the preferred versions contained herein, except where required by 35 U.S.C. § 112 ¶6 or 35 U.S.C. § 112 (f).

The reader's attention is directed to all references which are filed concurrently with this specification and which are incorporated herein by reference.

All the features in this specification (including any accompanying claims, abstract, and drawings) may be replaced by alternative features serving the same, equivalent or similar purpose, unless expressly stated otherwise. Thus, unless expressly stated otherwise, each feature disclosed in one example only of a generic series of equivalent of similar features. Any element in a claim that does not explicitly state "means for" performing a specified function, or "step for" performing a specific function, is not to be interpreted as a "means" or "step" clause as specified in 35 U.S.C. § 112 ¶6 or 35 U.S.C. § 112 (f). Any element in a claim that does explicitly state "means for" performing a specified function, or "step for" performing a specific function, is to be interpreted as a "means" or "step" clause as specified in 35 U.S.C. § 112 ¶6 or 35 U.S.C. § 112 (f).

What is claimed is:

1. An effective method for decontaminating an outer integument of an animal without transferring contamination to an inner integument of the animal, the method comprising:
    (a) providing a contaminated animal, wherein the contaminated animal has the outer integument comprising of either fur, hair, or feathers; wherein the animal has the inner integument comprising skin; and wherein a skin-hazard material is present on the outer integument;
    (b) providing a first porous dry wipe;
    (c) using the first porous dry wipe to sequester the skin-hazard material away from the contaminated animal by either wiping, blotting or rubbing the outer integument of the contaminated animal;
    (d) not using free-flowing liquid in contact with the inner integument of the contaminated animal;
    (e) not promoting a liquid-phase transfer of the skin-hazard material from the outer integument to the inner integument;
        wherein, the method does not comprise reacting, binding, oxidizing, hydrolyzing, or otherwise chemically detoxifying the skin-hazard material.

2. The method of claim 1, further comprising:
    (f) not using free-flowing liquid in contact with the inner integument, wherein the free-flowing liquid comprises a mixture of soap and water; and
    (g) not submersing any part of the contaminated animal in a liquid bath.

3. The method of claim 2, further comprising:
    wherein, the skin-hazard material is a skin contact-hazard material, and
    (h) effectively decontaminating the contaminated animal, wherein effectively decontaminating is defined as reducing a presence of the skin hazard material on the outer integument to a level below a contact-hazard level for the contaminated animal, and while not transferring an amount of the skin contact-hazard material, which is above a contact-hazard level for the animal, from the outer integument to the inner integument.

4. The method of claim 3, further comprising:
(i) using a wetted wipe to sequester at least a portion of the skin contact-hazard material away from the contaminated animal by either wiping, blotting or rubbing the outer integument of the contaminated animal.

5. The method of claim 4, further comprising:
(j) using the wetted wipe to deposit a skin-hazard material solubilizing agent onto the outer integument; and
(k) using a second porous dry wipe after using the wetted wipe to sequester at least a portion of the skin-hazard material away from the contaminated animal by either wiping, blotting or rubbing the outer integument containing the skin-hazard material solubilizing agent on the contaminated animal.

6. The method of claim 5, further comprising:
(l) trimming or cutting a portion of the outer integument off of the contaminated animal.

7. The method of claim 4, wherein the using the wetted wipe step happens after step (c).

8. The method of claim 4, wherein the wetted wipe contains water, water with a detergent or surfactant, or a solvent selected from the group consisting of turpentine, glycerol, polyethylene glycol, propylene carbonate, ethanol, 2-propoanol, toluene, kerosene, vegetable oil, and ethyl acetate.

9. The method of claim 8, wherein the wetted wipe contains linear, C12, secondary alcohol alkoxylate, polyoxyethylene (4) sorbitan monolaurate, octyldimethylamine oxide, and cocoamidopropyl dimethlamine oxide.

10. The method of claim 1, wherein the skin-hazard material is a presumed skin-hazard material.

11. An effective method for decontaminating the outer integument of an animal without transferring contamination to the inner integument of the animal, the method comprising:
(a) providing a contaminated animal, wherein the contaminated animal has an outer integument comprising of either fur, hair, or feathers; wherein the animal has an inner integument comprising skin; and wherein a skin-hazard material is present on the outer integument;
(b) providing a first porous wetted wipe;
(c) using the first porous wetted wipe to sequester the skin-hazard material away from the contaminated animal by either wiping, blotting or rubbing the outer integument of the contaminated animal;
(d) not using free-flowing liquid in contact with the inner integument of the contaminated animal; and
(e) not promoting a liquid-phase transfer of the skin-hazard material from the outer integument to the inner integument;
wherein, the method does not comprise reacting, binding, oxidizing, hydrolyzing, or otherwise chemically detoxifying the skin-hazard material.

12. The method of claim 11, further comprising:
(f) not using free-flowing liquid in contact with the inner integument, wherein the free-flowing liquid comprises a mixture of soap and water; and
(g) not submersing any part of the contaminated animal in a liquid bath.

13. The method of claim 12, further comprising:
wherein, the skin-hazard material is a skin contact-hazard material, and
(h) effectively decontaminating the contaminated animal, wherein effectively decontaminating is defined as reducing the presence of the skin hazard material on the outer integument to a level below a contact-hazard level for the contaminated animal, and while not transferring an amount of the skin contact-hazard material, which is above a contact-hazard level for the animal, from the outer integument to the inner integument.

14. The method of claim 13, further comprising:
(i) using a second wetted wipe to sequester at least a portion of the skin contact-hazard material away from the contaminated animal by either wiping, blotting or rubbing the outer integument of the contaminated animal.

15. The method of claim 14, further comprising:
(j) using the first wetted wipe to deposit a skin-hazard material solubilizing agent onto the outer integument; and
(k) using a second porous wetted wipe after using the first wetted wipe to sequester at least a portion of the skin-hazard material away from the contaminated animal by either wiping, blotting or rubbing the outer integument containing the skin-hazard material solubilizing agent, of the contaminated animal.

16. The method of claim 15, further comprising:
(l) trimming or cutting a portion of the outer integument off of the contaminated animal.

17. The method of claim 16, wherein the first wetted wipe contains selected from the group consisting of turpentine, glycerol, polyethylene glycol, propylene carbonate, ethanol, 2-propoanol, toluene, kerosene, vegetable oil, and ethyl acetate.

18. The method of claim 17, wherein the first wetted wipe contains linear, C12, secondary alcohol alkoxylate, polyoxyethylene (4) sorbitan monolaurate, octyldimethylamine oxide, and cocoamidopropyl dimethlamine oxide.

19. The method of claim 18 wherein the second wetted wipe contains water or solvent without skin-hazard material solubilizing agent.

20. The method of claim 11, wherein the skin-hazard material is a presumed skin-hazard material.

* * * * *